(12) United States Patent
Olson

(10) Patent No.: US 11,986,638 B2
(45) Date of Patent: May 21, 2024

(54) SAFETY MECHANISM FOR A MEDICAMENT DELIVERY DEVICE AND A MEDICAMENT DELIVERY DEVICE COMPRISING THE SAME

(71) Applicant: SHL MEDICAL AG, Zug (CH)

(72) Inventor: Stephan Olson, Danderyd (SE)

(73) Assignee: SHL Medical AG, Zug (CH)

( * ) Notice: Subject to any disclaimer, the term of this patent is extended or adjusted under 35 U.S.C. 154(b) by 410 days.

(21) Appl. No.: 17/391,863

(22) Filed: Aug. 2, 2021

(65) Prior Publication Data

US 2021/0361873 A1 Nov. 25, 2021

Related U.S. Application Data

(63) Continuation of application No. 16/070,615, filed as application No. PCT/EP2017/051159 on Jan. 20, 2017, now Pat. No. 11,141,533.

(30) Foreign Application Priority Data

Feb. 24, 2016 (SE) .................................... 1650247-8

(51) Int. Cl.
*A61M 5/32* (2006.01)
*A61M 5/31* (2006.01)

(52) U.S. Cl.
CPC .............. *A61M 5/31* (2013.01); *A61M 5/326* (2013.01); *A61M 2005/3143* (2013.01)

(58) Field of Classification Search
CPC ...... A61M 2005/3143; A61M 5/31521; A61M 5/31523; A61M 5/326; A61M 5/3202;
(Continued)

(56) References Cited

U.S. PATENT DOCUMENTS 3,882,863 A 5/1975 Sarnoff et al.
9,757,520 B2 9/2017 Corrigan et al.
(Continued)

FOREIGN PATENT DOCUMENTS

CN 103239780 A 8/2013
FR 2990353 A1 11/2013
(Continued)

OTHER PUBLICATIONS

International Search Report and Written Opinion for Int. App. No. PCT/EP2017/051159, mailed Apr. 19, 2017.
(Continued)

*Primary Examiner* — Deanna K Hall
(74) *Attorney, Agent, or Firm* — McDonnell Boehnen Hulbert & Berghoff LLP

(57) ABSTRACT

The present disclosure relates to a safety mechanism for a medicament delivery device for mechanical shock absorption, which safety mechanism has a medicament delivery member sleeve, a housing having a proximal opening arranged to receive the medicament delivery member sleeve, wherein the medicament delivery member sleeve is axially displaceable inside the housing, between an extended position in which a proximal end portion of the medicament delivery member sleeve extends proximally from the housing and a retracted position in which the proximal end portion is received by the housing, wherein the proximal end portion has a resilient structure, enabling compression of the proximal end portion in the distal direction upon impact of an axial force greater than a threshold value.

20 Claims, 5 Drawing Sheets

(58) Field of Classification Search
CPC ........ A61M 5/3243; A61M 2005/3247; A61M 2005/3267; A61M 5/2033; A61M 5/31571
See application file for complete search history.

(56) References Cited

U.S. PATENT DOCUMENTS

| | | |
|---|---|---|
| 2003/0236502 A1 | 12/2003 | De La Serna et al. |
| 2007/0219498 A1 | 9/2007 | Malone et al. |
| 2012/0010574 A1 | 1/2012 | Takemoto et al. |
| 2014/0148763 A1* | 5/2014 | Karlsson ............... A61M 5/326 604/221 |
| 2014/0343507 A1 | 11/2014 | Karlsson et al. |

FOREIGN PATENT DOCUMENTS

| | | |
|---|---|---|
| GB | 2506918 A | 4/2014 |
| JP | 2014-519923 A | 8/2014 |
| JP | 2014519922 A | 8/2014 |
| TW | M511868 U | 11/2015 |
| TW | I517871 B | 1/2016 |
| TW | M514857 U | 1/2016 |
| TW | I519331 B | 2/2016 |
| TW | I520757 B | 2/2016 |
| TW | M516983 U | 2/2016 |
| WO | 2015/062845 A1 | 5/2015 |
| WO | 2015/101487 A1 | 7/2015 |
| WO | 2015/150578 A1 | 10/2015 |
| WO | 201625327 A1 | 2/2016 |

OTHER PUBLICATIONS

Chinese Office Action for CN Application No. 201780010655.9, issued Mar. 10, 2021.

* cited by examiner

SAFETY MECHANISM FOR A MEDICAMENT DELIVERY DEVICE AND A MEDICAMENT DELIVERY DEVICE COMPRISING THE SAME

CROSS REFERENCE TO RELATED APPLICATIONS

The present application is a continuation of U.S. patent application Ser. No. 16/070,615, filed Jul. 17, 2018, which is a U.S. National Phase Application pursuant to 35 U.S.C. § 371 of International Application No. PCT/EP2017/051159 filed Jan. 20, 2017, which claims priority to Swedish Patent Application No. 1650247-8 filed Feb. 24, 2016. The entire disclosure contents of these applications are herewith incorporated by reference into the present application.

TECHNICAL FIELD

The present disclosure generally relates to medical devices. In particular, it relates to medicament delivery devices.

BACKGROUND

Some medicament delivery devices have a medicament delivery member cover which by movement, e.g. linear displacement, activates medicament expulsion. An example of such a medicament delivery device is disclosed in US2014/0148763 A.

The injection device disclosed in US2014/0148763 A1 is activated by linear displacement of a needle shield sleeve. The needle shield sleeve is displaceable between an extended position and a retracted position relative to the housing of the injection device. Moreover, the needle shield sleeve is biased towards the extended position so that prior to medicament expulsion, the needle shield sleeve is in the extended position. Linear motion of the needle shield sleeve in the distal direction, i.e. towards its retracted position, is transformed to rotational motion of a container driver locking means which due to rotation releases a medicament container holder, enabling medicament expulsion therefrom. The needle shield sleeve is biased in the proximal direction of the injection device. The needle shield will therefore return to its extended position when the injection device is removed from the injection site. Moreover, the needle shield sleeve engages with the container driver locking means such that the needle shield sleeve is locked in the extended position.

When the needle shield sleeve is locked in a final position mechanical shock may damage the means by which it obtains its locked extended position, thereby leading to exposure of the medicament delivery member. Such a situation may for example occur in case the medicament delivery member is dropped and hits a hard support surface, especially if the device has an essentially vertical orientation upon impact.

SUMMARY

A general object of the present disclosure is to provide a safety mechanism for a medicament delivery device, and a medicament delivery device comprising such safety mechanism, which solve or at least mitigate the above-mentioned problem of the prior art.

There is hence according to a first aspect of the present disclosure provided a safety mechanism for a medicament delivery device for mechanical shock absorption, which safety mechanism comprises: a medicament delivery member sleeve, a housing having a proximal opening arranged to receive the medicament delivery member sleeve, wherein the medicament delivery member sleeve is axially displaceable inside the housing, between an extended position in which a proximal end portion of the medicament delivery member sleeve extends proximally from the housing and a retracted position in which the proximal end portion is received by the housing, wherein the proximal end portion has a resilient structure, enabling compression of the proximal end portion in the distal direction upon impact of an axial force greater than a threshold value.

Due to the proximal end portion, and thus the medicament delivery member sleeve being deformable upon impact of a large enough axial force, mechanical shock may be absorbed.

According to one embodiment the proximal end portion is arranged to expand radially upon compression, to a radial dimension greater than the corresponding dimension of the proximal opening. Due to the radial expansion, the medicament delivery member sleeve will be prevented from obtaining its retracted position, which would expose the medicament delivery member. To this end, the medicament delivery member sleeve will maintain a position in which it covers the medicament delivery member even upon being subjected to a relatively large mechanical shock, damaging means that maintain the medicament delivery member sleeve in the extended position after medicament expulsion.

According to one embodiment the proximal end portion is tubular and has a weakened sidewall.

According to one embodiment the weakened sidewall comprises through-openings extending in the peripheral direction.

According to one embodiment the through-openings extend along a majority of the periphery of the proximal end portion.

According to one embodiment the through-openings form a system of through-opening configured to enable axial deformation of the medicament delivery member sleeve.

According to one embodiment the system of through-openings includes two oppositely arranged central through-openings, and a first pair and a second pair of elongated through-openings, each of the first pair and the second pair of elongated through-opening being axially displaced relative to each other, mirrored in a radial plane, on opposite sides of the central through-openings, wherein the first pair and the second pair of through-openings are mirrored in an axial plane.

According to one embodiment the medicament delivery member sleeve is arranged to elastically deform upon compression and radial expansion.

According to one embodiment the medicament delivery member sleeve is arranged to plastically deform upon compression and radial expansion.

One embodiment comprises a container driver locking member rotatable from a first rotational position to a second rotational position, and a first energy accumulating member arranged to bias the medicament delivery member sleeve in the proximal direction, wherein the medicament delivery member sleeve and the container driver locking member are configured such that linear motion of the medicament delivery member sleeve from the extended position to the retracted position is transformed into rotational motion of the container driver locking member from the first rotational position to the second rotational position, wherein the container driver locking member is configured to allow the medicament delivery member sleeve to return to the extended position, and to restrict movement of the medicament delivery member sleeve when the container driver locking member is in the second rotational position.

One embodiment comprises a proximal flange provided at the proximal end of the medicament delivery member sleeve, which proximal flange has a first radially flexible arm extending longitudinally in the distal direction, and wherein the housing has a proximal portion arranged between the first radially flexible arm and the outer surface of the medicament delivery member sleeve when the medicament delivery member sleeve is displaced from the extended position to the retracted position, a cover having a distal opening forming a channel arranged to receive the medicament delivery member sleeve and the housing, wherein the channel is dimensioned such that, when the housing is received by the cover, there is a radial distance between the inner surface of the cover and the outer surface of the proximal portion which is less than a radial dimension of the first radially flexible arm, preventing the medicament delivery member sleeve from obtaining its retracted position.

Due to there being a radial distance between the inner surface of the cover and the outer surface of the proximal portion, which is less than a radial dimension of the first radially flexible arm, the first radially flexible arm will not be able to reach its retracted position for activating medicament expulsion, in the event of mechanical shock/impact with a force directed generally in the axial direction.

According to one embodiment the first radially flexible arm is arranged to bear against the outer surface of the proximal portion in the retracted position.

According to one embodiment the proximal flange has a body, wherein the first radially flexible arm extends from the body, from a radial distance corresponding to the radial dimension of the outer surface of that portion of the proximal end of the housing which is axially aligned with the first radially flexible arm.

According to one embodiment the first radially flexible arm is inclined relative to the central axis of the medicament delivery member sleeve.

According to a second aspect there is provided a medicament delivery device comprising a safety mechanism according to the first aspect.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The medicament delivery device disclosed herein may for example a disposable single-use medicament delivery device, such as an auto-injector, an inhaler or an eye dispenser. The medicament delivery device may be a regular medicament delivery device for medicament administration, or a trainer device.

The term "proximal end" as used herein refers to that end of a medicament delivery device at which medical expulsion can be provided. This is hence that end of the medicament delivery device that is to be pointed towards the injection or expulsion site. This definition also extends to any internal or external component of the medicament delivery device, i.e. the proximal end of any component is that which is closest to the proximal end of the medicament delivery device. The "distal end" is the opposite end relative to the proximal end. With "proximal direction" is meant a direction from the distal end towards the proximal end, along the central axis of the medicament delivery device. With "distal direction" is meant the opposite direction to "proximal direction".

Figure 1A:
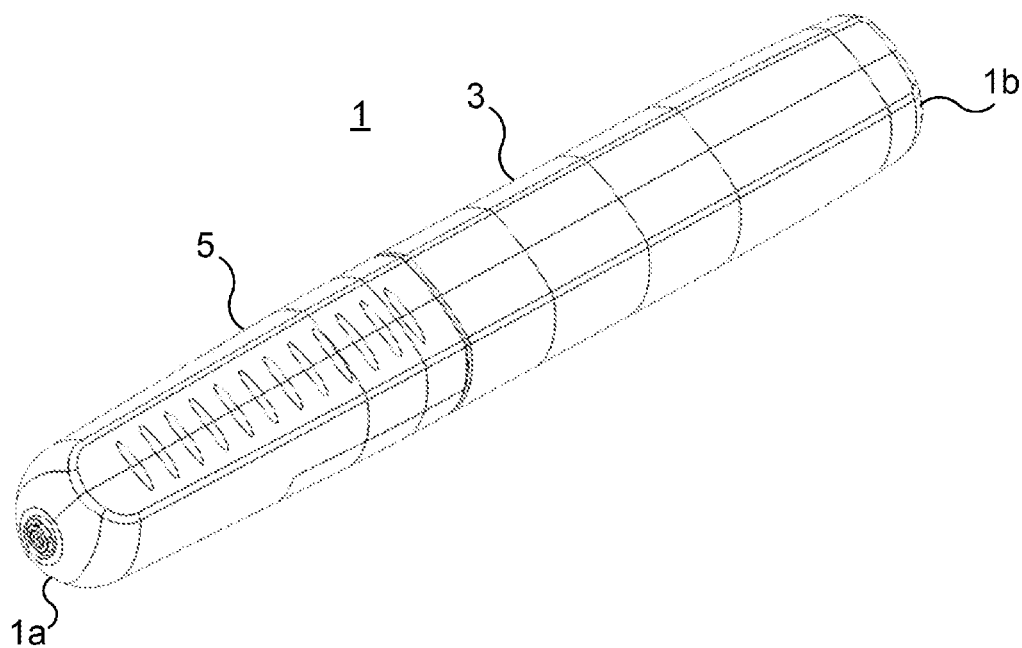
FIGS. 1a and 1b are perspective views of an example of a medicament delivery device.

FIG. 1a shows an example of a medicament delivery device including a safety mechanism for preventing activation of the medicament delivery device in the event of mechanical shock.

Medicament delivery device 1, which is an auto-injector, is an example of a medicament delivery device comprising a safety mechanism. It should be understood that other realisations of a medicament delivery device comprising a safety mechanism as disclosed herein are also envisaged.

In FIG. 1a, the exemplified medicament delivery device 1 has a proximal end 1a and a distal end 1b, and comprises a housing 3 and a proximally arranged cover 5 for concealing the medicament delivery member mounted inside the medicament delivery device 1. The housing 3 may be formed of one or more housing parts.

Figure 1B:
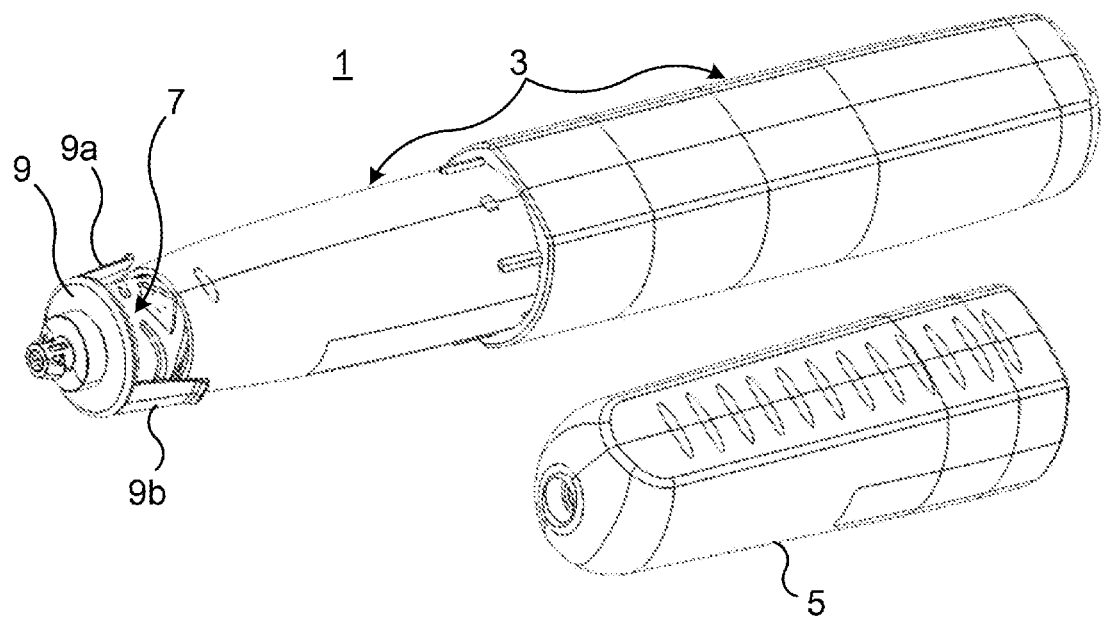

FIG. 1b shows the medicament delivery device 1 with its cover 5 removed. The medicament delivery device 1 furthermore includes a medicament delivery member sleeve 7, arranged to cover a medicament delivery member such as a needle, and received in a central proximal opening of the housing 3, and axially displaceable relative to the housing 3 between an extended position shown in FIG. 1b and a retracted position.

The medicament delivery device 1 also includes a proximal flange 9 provided at the proximal end of the medicament delivery member sleeve 7. The proximal flange 9 may either be mounted as a separate part to the medicament delivery sleeve member 7, or it may be integrated therewith. The proximal flange 9 has a first radially flexible arm 9a and a second radially flexible arm 9b, both arms 9a and 9b extending longitudinally in the distal direction.

According to one aspect the proximal flange 9 with its first and second radially flexible arms 9a, 9b, the medicament delivery member sleeve 7, the housing 3 and the cover 5 form a safety mechanism. According to another aspect the medicament delivery member sleeve 7 and the housing 3 form the safety mechanism. Both aspects will be described in more detail in the following. However, before describing the structure and operation of the safety mechanism in more detail, the general structure and function of the exemplified medicament delivery device will be described.

Figure 2:
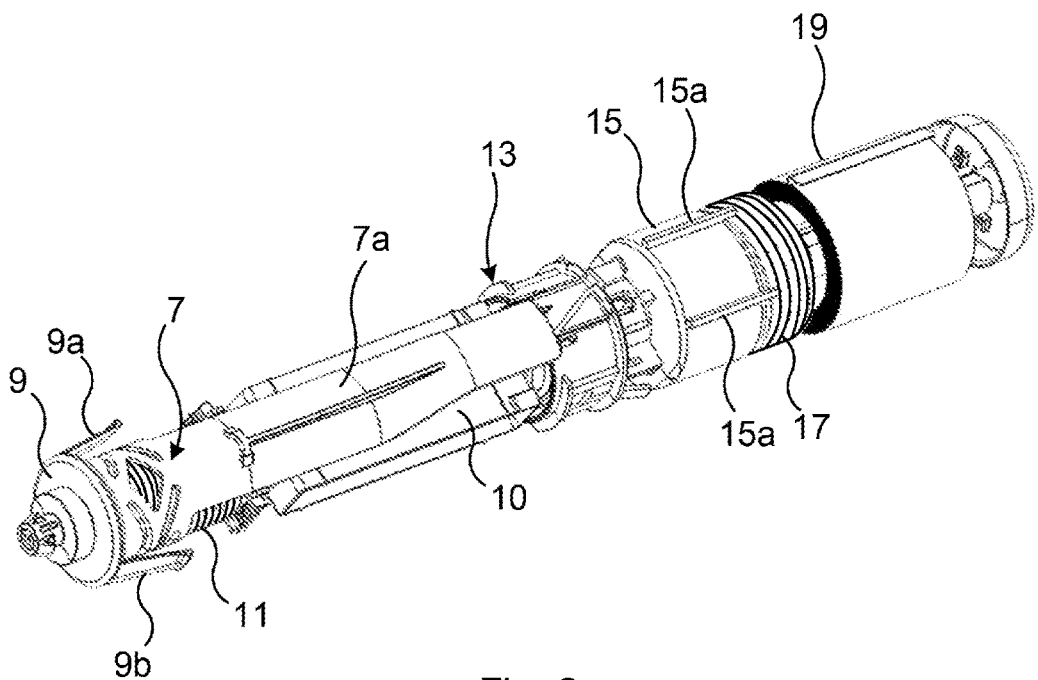
FIG. 2 shows a perspective view of some assembled internal components of the medicament delivery device in FIGS. 1a and 1b.
Figure 3:
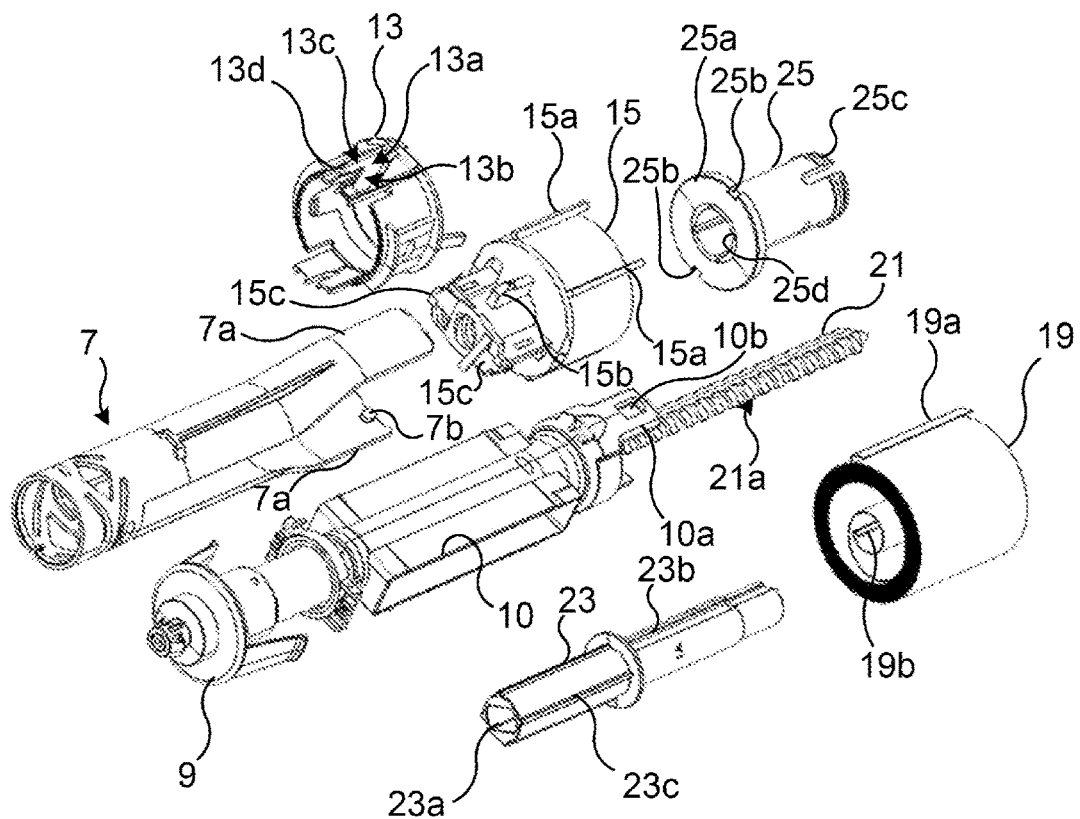
FIG. 3 shows a perspective view of some internal components, here partially separated from each other, of the components shown in FIG. 2.

With reference to FIGS. 2 and 3, certain internal components of the medicament delivery device 1 are here depicted. The exemplified medicament delivery member sleeve 7 comprises two tongue extensions 7a, of which only one is shown in FIG. 2, forming the distal end portion of the medicament delivery member sleeve 7. The tongue extensions 7a are arranged on opposite sides, relative to the longitudinal central axis of the medicament delivery device 1. The tongue extensions 7a are hence arranged in a common plane containing the longitudinal central axis. According to the example, the proximal portion of medicament delivery member sleeve 7 is of generally cylindrical form.

In the example shown in the drawings, the tongue extensions 7a essentially comprise three axial section or axial portions. The first, most proximal portion is formed by two cylinder segments having the same radius/diameter as the cylindrical most proximal portion of medicament delivery member sleeve 7. The distal end of tongue extensions 7a are spaced from each other at a greater distance than the diameter of the cylinder segments portion. In between these two portions, an intermediate portion is provided that forms a transition between the smaller diameter of the cylinder segments portion and the greater distance at the distal end of the tongue extensions 7a. In general terms, the medicament delivery member sleeve 7 has a widened configuration in that it widens from the proximal end towards the distal end thereof.

The medicament delivery member sleeve 7 is biased, or pre-tensioned, in the proximal direction. To this end, the medicament delivery device 1 includes a first energy accumulating member 11, e.g. a compression spring, arranged to bias the medicament delivery member sleeve 7 in the proximal direction. The default position of the medicament delivery member sleeve 7 is hence the extended position.

The medicament delivery member 1 comprises a container driver locking member 13, a container driver 15, and a container holder 10. The exemplified container holder 10 is arranged to hold a medicament container assembly including a medicament container and a needle. Moreover, the container holder 10 is linearly displaceable but rotationally locked relative to the housing 3.

The container driver locking member 13 is arranged to mechanically interact with the medicament delivery member sleeve 7. In particular, linear displacement of the medicament delivery member sleeve 7, from the extended position to the retracted position, is transformed to rotational motion of the container driver locking member 13, from a first rotational position to a second rotational position, as will be described in the following.

The container driver locking member 13 is generally ring-shaped. Container driver locking member 13 is rotatable in relation to the housing 3 and in engagement with the medicament delivery member sleeve 7.

Container driver locking member 13 has two opposing external groove structures 13a, of which one is shown in FIG. 3. Each groove structure 13a has two segments, namely an inclined groove 13b and a longitudinal groove 13c. In the initial extended position of the medicament delivery member sleeve 7, radial protrusions 7b provided on the inner surface of the distal end portion of the tongue extensions 7a are arranged in the inclined groove 13b of the groove structures 13a. When the proximal end face 70 of the medicament delivery device 1 is placed on an injection site, for example the skin of a user, the medicament delivery member sleeve 7 is thereby pushed or moved towards its retracted position. Such displacement of the medicament delivery member sleeve 7 causes the protrusions 7b to move in the inclined grooves 13a towards the distal end of the container driver locking member 13. Since the container driver locking member 13 is rotatable in relation to the housing 3 but longitudinally fixed because it proximally bears against the container driver 15, and the medicament delivery member sleeve 7 is rotationally locked, longitudinal displacement of the medicament delivery member sleeve 7 towards the distal end of the medicament delivery device 1 results in a rotational movement of the container driver locking member 13 from the first rotational position towards the second rotational position, allowing the protrusions 7b to slide towards the distal ends of inclined grooves 13b.

As long as the medicament delivery device 1 is pressed towards the injection site, i.e. as long as the medicament delivery member sleeve 7 is held in its retracted position, the protrusions 7b stay at the distal end of the groove structures 13a. However, when the user removes the medicament delivery device 1 from the injection site, for example after medicament delivery, the medicament delivery member sleeve 7 is urged towards the extended position, as described above. During this movement, the projections 7b slide along longitudinal grooves 13c and are locked at the proximal ends of the longitudinal grooves 13c by respective locking structures 13d. This prevents that the medicament delivery member sleeve 7 can again be moved towards the retracted position.

The container driver 15 is arranged distally from the container driver locking member 13. Container driver 15 is arranged to be connectable to the container holder 10. The container driver 15 is linearly displaceable but rotationally locked relative to the housing 3. The container driver 15 may to this end be provided with for example rotational locking ribs 15a arranged to engage with corresponding grooves provided on the inner surface of the housing 3. In the present example, four rotational locking ribs 15a are provided, three of which are shown in FIG. 3. The locking ribs as well as the corresponding grooves extend in the longitudinal direction. Such structure prevents the container driver 15 from being rotated, i.e. the container driver 15 is movable in the longitudinal direction relative to the housing but rotationally locked.

At its proximal side, the container driver 15 comprises at least one container driver arm 15b. According to the example, the container driver 15 has two container driver arms 15b, arranged in a common plane containing the longitudinal central axis of the medicament delivery device 1. The container driver arms 15b are configured for engagement with corresponding radial openings 10b provided in a container holder tongue extensions 10a provided at the distal end of the container holder 10. Thus, the container holder 10 is connected with the container driver 15. Longitudinal displacement of the container driver 15 towards the proximal end of the medicament delivery device 1 results in a movement of the container holder 10 towards the proximal end of the medicament delivery device 1 whereby a needle penetration is performed.

The container driver 15 comprises at least one ledge 15*c*. According to the example, two ledges 15*c* are provided. With these ledges 15*c*, the container driver 15 initially abuts against stop ribs provided on the inner surface of the container driver locking member 13. Thus, in the initial extended position of the medicament delivery member sleeve 7, i.e., prior to its use, the container driver 15 and thus the container holder 10 are prevented from being moved proximally because such movement is blocked by the container driver locking member 13 due to the abutment of the ledges 15*c* against the stop ribs. Only upon rotational movement of the container driver locking member 13, caused by distal displacement of the medicament delivery member sleeve 7, the stop ribs are moved out of abutment with the ledges 15*c*. Thus, the container driver is no longer axially locked/blocked by container driver locking member 13.

The medicament delivery device 1 furthermore comprises a plunger rod 21, a plunger driver 23, a plunger driver locking member 25, a second energy accumulating member 17, and a third energy accumulating member 19.

The second energy accumulating member 17 is arranged to bias the container driver 15 in the proximal direction. The second energy accumulating member 17 may for example be a compression spring.

The third energy accumulating member 19 may for example be a torsional spring. The third energy accumulating member 19 has an outer end 19*a* which connects the third energy accumulating member 19 to the housing 3 and an inner end 19*b* which connects the third energy accumulating member 19 to the plunger driver 23. The outer end 19*a* may, for example, extend through a longitudinal slit in the housing 3 so that it may be engaged with the wall in the form of a hook.

The plunger driver locking member 25 is of generally cylindrical configuration and has a radial flange 25*a* at its proximal end. The radial flange 25*a* comprises at least one rotational locking structure 25*b*. According to the example the rotational locking structure 25*b* is defined by a radial recess but could alternatively for example be defined by a radial projection. In the example shown in FIG. 3, two such rotational locking structures 25*b* are provided. With these rotational lockers structures 25*b*, the plunger driver locking member 25 is initially rotationally locked to the container driver 15. In order to provide such rotational locking, the container driver 15 has corresponding longitudinal ribs at the inner surface of its distal portion. The rotational locking structures 25*b* initially abut against these longitudinal ribs. The axial length of these locking ribs of the container driver 15 is adapted to the length the container driver 15 and the container holders 10 are displaced/displaceable to perform a needle penetration. In more detail, the axial length of the longitudinal ribs is such that upon full displacement of the container holder 10 in the proximal direction, the rotational lockers 25*b* are finally freed from engagement with the longitudinal ribs. This means that at this stage the plunger driver locking member 25 is no longer rotationally locked by the container driver 15. In other words, when performing needle penetration, the container holder 15 is moved longitudinally relative to the plunger driver locking member 25. The plunger driver locking member 25 is axially locked. Such axial lock is provided by an axial locking structure 25*c* at the distal end of the plunger driver locking member 25 which is in engagement with a corresponding structure at a distal end of the housing 3.

The plunger rod 21 has a threaded structure 21*a* and has a non-circular cross-sectional shape.

The plunger driver 23 is rotationally locked to the plunger driver locking member 25 but slidable in the axial direction in relation to the plunger driver locking member 25. The exemplified plunger driver 23 has a longitudinally extending through-opening 23*a* arranged to receive the plunger rod 21. To this end, the through-opening 23*a* has a non-circular cross-sectional shape, in particular the same cross-sectional shape as the plunger rod 21 has. Thus, the plunger rod 21 is rotationally locked to the plunger driver 23 but may axially slide inside the through-opening 23*a*.

Plunger driver 23 furthermore has a longitudinal slit 23*b* provided in the external surface thereof. With this longitudinal slit 23*b*, the plunger driver 23 is connected to the inner end 19*b* of the third energy accumulating member 19. Thus, a force applied to the plunger driver 23 by the third energy accumulating member 19 is transmitted to the plunger rod 21 due to the engagement with the plunger driver 23.

The plunger driver 23 comprises at least one external longitudinal rib 23*c*. According to the example in FIG. 3, four such longitudinal ribs 23*c* are provided spaced at 90° to each other. The external longitudinal ribs 12*c* are slidably received in longitudinal grooves 25*d* of the plunger driver locking member 25. Thus, as long as the plunger driver locking member 25 is prevented from being rotated due to the locking engagement with the container driver 15, the plunger driver 23 and the plunger rod 21 are prevented from being rotated although the force of the third energy accumulating member 19 acts on the plunger driver 23. However, once the plunger driver locking member 25 is free to rotate, the plunger driver 23 and the plunger rod 21 also start to rotate, concurrently, caused by the third energy accumulating member 19.

In the initial state of the medicament delivery device 1, i.e. prior to its use, a proximal portion of the plunger rod 21 is received in the central opening of the container driver 15. The central opening of container driver 15 comprises a threaded structure that engages with the external threads of the plunger rod 21. Thus, the threaded proximal portion of the plunger rod 21 is screw threaded in the interior of the container driver 15. Due to this threaded engagement, rotation of the plunger rod 21 upon use of the medicament delivery device 1 results in an axial displacement of the plunger rod 21 towards the proximal end 1*a* of the medicament delivery device 1. In other words, the plunger rod 21 is rotated by the thread engagement in the direction of the medicament container 10, and causes a stopper in the container holder 10 to move towards the proximal end of the container holder 10 in order to expel medicament from the medicament container arranged in the container holder. The torque force of energy accumulating member 19 will continue to drive the plunger rod 21 towards the proximal end 1*a* of the medicament delivery device 1, pressing the stopper to expel medicament through the needle. The container driver 15 slides over along the plunger rod 21 as the plunger rod 21 continues to move towards the proximal end 1*a* of the medicament delivery device 1. The injection is completed when the stopper is at the proximal end of the medicament container.

Figure 4:
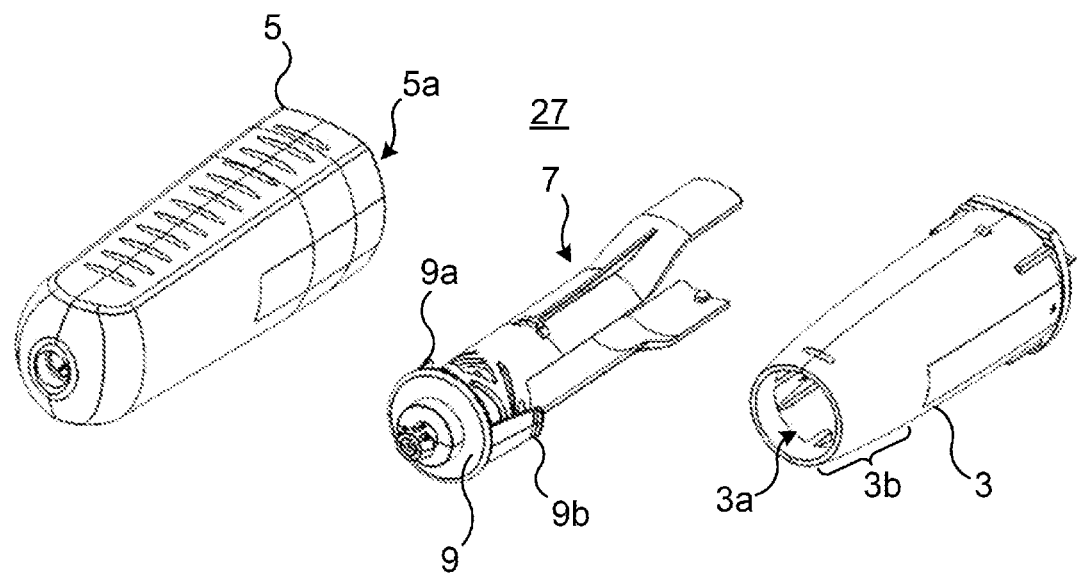
FIG. 4 is a perspective view of an example of a safety mechanism of the medicament delivery device in FIG. 1.

Turning now to FIG. 4, an example of the safety mechanism will now be described. As previously noted, according to one aspect the safety mechanism 27 includes the cover 5, the medicament delivery member sleeve 7, the proximal flange 9, and the housing 3, which according to the present example is a proximal housing part.

The housing 3 has a central proximal opening 3a in which the medicament delivery member sleeve 7 is arranged to be received. The cover 5 is hollow and has a central distal opening 5a, which cannot be seen in FIG. 4, forming a channel arranged to receive the medicament delivery member sleeve 7 and the proximal part/portion of the housing 3. When medicament is to be administration, the cover 5 is removed to expose the medicament delivery member sleeve 7 and the proximal part/portion of the housing 3 previously covered by the cover 5. In this exposed state, i.e. when the cover 5 has been removed, the medicament delivery member sleeve 7 is axially displaceable between a default initial extended position relative to the housing 3, and a retracted position. This functionality and its effect on medicament expulsion have already been explained above.

Figure 5:
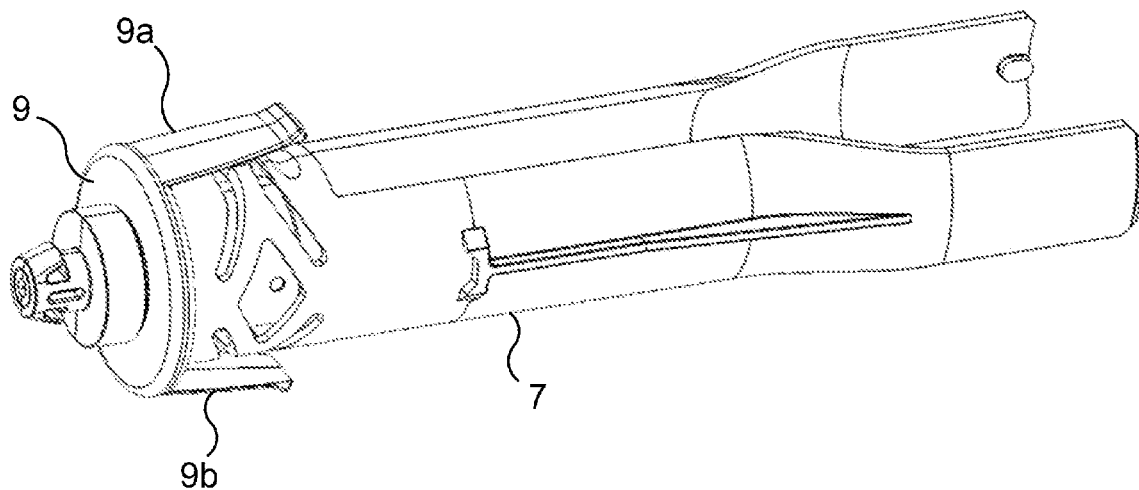
FIG. 5 is a perspective view of medicament delivery member sleeve and proximal flange of the safety mechanism in FIG. 4.

FIG. 5 shows the medicament delivery member sleeve 7 and the proximal flange 9 in more detail. The proximal end of the medicament delivery member sleeve 7 is provided with the proximal flange 9. The exemplified proximal flange 9 has a first radially flexible arm 9a and a second radially flexible arm 9b extending longitudinally in the distal direction. Each of the first radially flexible first arm 9a and the second radially flexible arm 9b are resilient in the radial direction. The first radially flexible arm 9a and the second radially flexible arm 9b are preferably arranged in the same plane containing the central axis of the medicament delivery device 1. In other words, the two radially flexible arms 9a and 9b are arranged at 180 degrees apart.

The proximal flange 9 has a body from which the first radially flexible first arm 9a and the second radially flexible arm 9b extend. Their base, at which they are connected to the body, is preferably at a radial distance from the central axis of the medicament delivery member sleeve 7, which is equal to or greater than the corresponding outer dimension of the proximal end of the housing 3. The first radially flexible arm 9a and the second radially flexible arm 9b extend towards the proximal end of the housing 3 and are arranged such that the housing 3, in particular a proximal portion 3b of the housing 3, is arranged between the outer surface of a proximal portion of the medicament delivery member sleeve 7 and the inner surface of each of the first radially flexible arm 9a and the second radially flexible arm 9b when the medicament delivery member sleeve 7 is displaced towards the retracted position. The first radially flexible arm 9a and the second radially flexible arm 9b may extend for example at least two thirds of the distance to the proximal end of the housing 3 when the medicament delivery member sleeve 7 is in the extended position. The first radially flexible arms 9a and the second radially flexible arm 9b may for example extend three thirds of the distance, or even distally beyond the proximal end of the housing 3 already in the retracted position of the medicament delivery member sleeve 7.

The first radially flexible arm 9a and the second radially flexible arm 9b may be inclined relative to the central axis of the medicament delivery device 1, with the distance from the central axis to the inner surface of the radially flexible arms 9a, 9b increasing in the distal direction. The proximal portion 3b of the housing 3 may widen in width in the distal direction, i.e. it may be tapering in the proximal direction.

Figure 6:
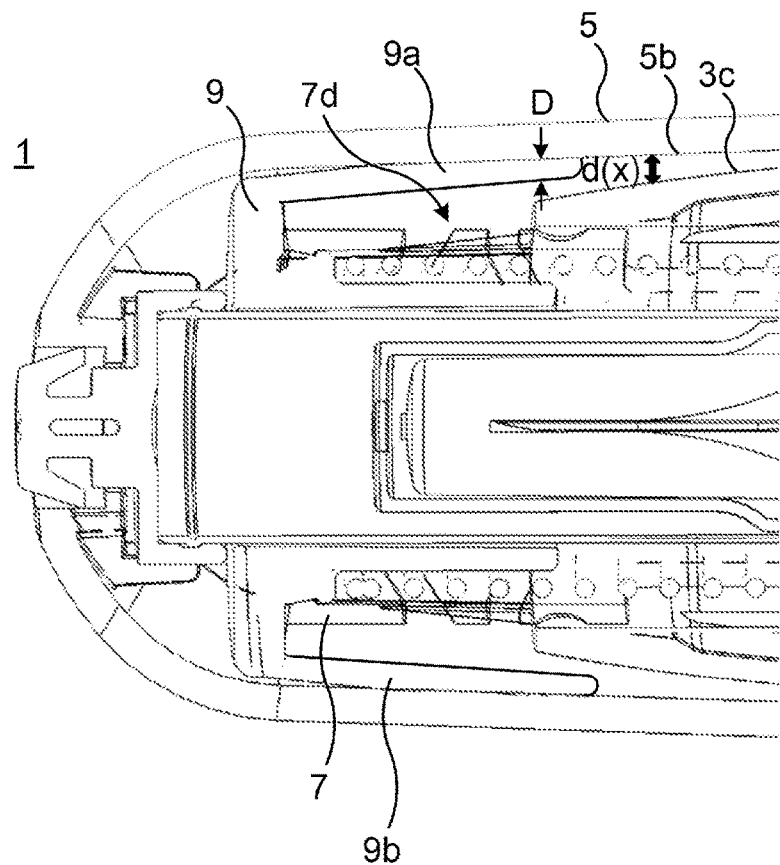
FIG. 6 is a longitudinal section of a proximal portion of the medicament delivery device in FIG. 1.

The inner dimensions of the channel formed in the cover 5 and the outer dimensions of the proximal portion 3b of housing 3 are designed so that the distance d(x) between the inner surface 5b of the cover 5 and the outer surface 3c of the housing 3 decreases in the distal direction when the cover 5 is properly mounted to the housing 3, as shown in FIG. 6. "x" is here a variable describing position along the central axis of the medicament delivery device 1. Moreover, the first radially flexible arm 9a and the second radially flexible arm 9b are designed so that their radial dimension D, at their distal end, is greater than a distance between the inner surface 5a of the cover 5 and the outer surface 3c of the proximal portion 3b. Initially, i.e. at the proximal end of the housing 3, the distance between the inner surface 5b of the cover 5 and the outer surface 3c of the proximal portion 3b is large enough for each of the first radially flexible arm 9a and the second radially flexible arm 9b to slide between the cover 5 and the proximal portion 3b of the housing 3 in the event that the medicament delivery member sleeve 7 is displaced a short distance from the extended position towards the retracted position. However, the distance between the inner surface 5b of the cover 5 and the outer surface 3c of the proximal portion 3b is preferably successively decreased so that further movement of the medicament delivery member sleeve 7 towards the retracted position results in that the first radially flexible arm 9a and the second radially flexible arm 9b are wedged between the cover 5 and the proximal portion 3b of the housing 3, prior to reaching the retracted position. In this manner, the medicament delivery member sleeve 7 is prevented from reaching its retraced position as long as the cover 5 is properly mounted to the housing 3. Thus in the event of mechanical shock, in particular when the medicament delivery device 1 is subjected to an impact at one of the proximal end 1a and the distal end 1b, movement of the medicament delivery member sleeve 7 is restricted, preventing accidental activation of the medicament delivery device 1.

It should be noted that as alternatives to the above example the safety mechanism 27 may comprise only one of the radially flexible arms, or the radially flexible arms could be located at other angles than 180 degrees apart.

According to the example shown in FIGS. 4-7, the safety mechanism provides one further safety aspect in addition to the safety aspect described above. The safety aspect describe above relates to prevention of accidental activation of the medicament delivery device 1, i.e. a prior use safety mechanism. In the following, a post-administration safety aspect will be described. This feature prevents accidental exposure of the medicament delivery member, e.g. a needle, after medicament administration, which could result from mechanical shock.

Figure 7:
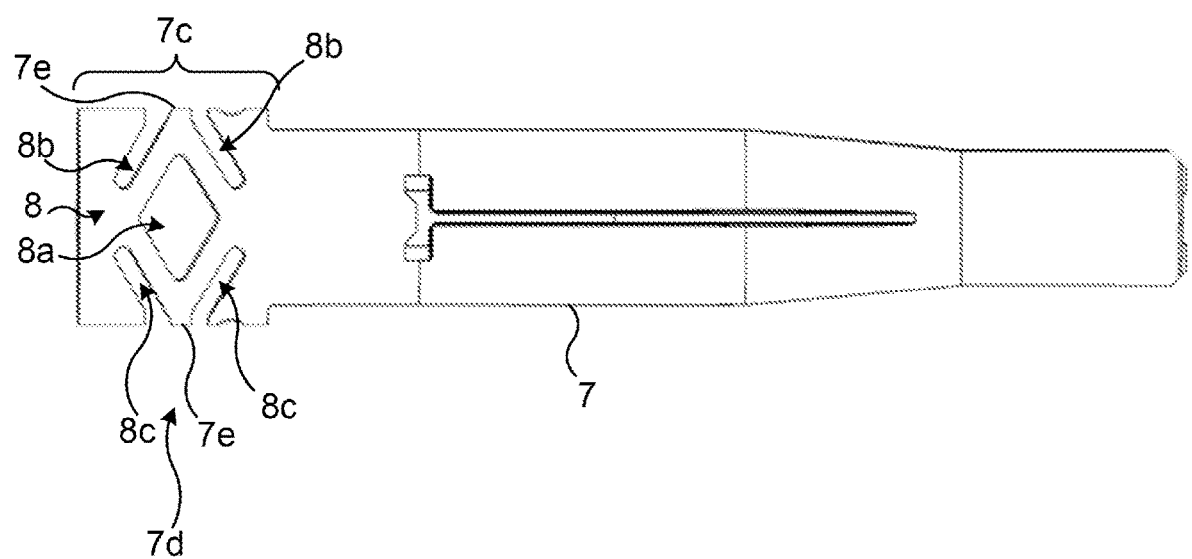
FIG. 7 is a side view of the medicament delivery member sleeve in FIG. 5.

With reference to FIG. 7 the medicament delivery member sleeve 7 has a proximal end portion 7c which has a resilient structure 7d, having a weakened mechanical strength, enabling compression of the proximal end portion in the distal direction upon impact of an axial force greater than a threshold or threshold value. The resilient structure 7d is furthermore arranged to expand radially upon compression so that the proximal end portion 7c obtains a radial dimension greater than a corresponding dimension of the proximal opening 3a of the housing 3.

The proximal end portion 7c is arranged outside of the housing 3, i.e. it extends proximally from the proximal opening 3a, when the medicament delivery member sleeve 7 is in the extended position.

The resilient structure 7d may be defined by a system of through-openings 8 which are arranged to provide the function of axial resilience of the medicament delivery member sleeve 7. To this end, the proximal end portion 7c has a weakened sidewall. According to the present example, the system of through-openings 8 comprises two oppositely arranged central through-openings 8a, of which only one can be seen in the drawings, and plurality of elongated through-openings 8b, 8c arranged laterally axially with respect to the central through-openings 8a. A first pair of through-openings 8b extend in the tangential direction, peripherally, partially surrounding the central through-openings 8a, and a second pair of through-openings 8c mirroring, in a plane containing the central axis of the medicament delivery device 1, the first pair of through-openings 8b. According to the example the central through-openings 8a are essentially rhomboid-shaped, and the trough-openings 8b and 8c follow the contours of the central through-openings 8a. In this manner narrow side wall bands 7e of the medicament delivery member sleeve 7 are formed in the axial direction between the pairs of through-openings 8b and 8c. These narrow side wall bands 7e are expanded radially when the resilient structure 7d is compressed.

The medicament delivery member sleeve 7 may for example be made of an elastically deformable plastic material, which thus obtains its original shape after compression, or it may be made of a plastically deformable plastic material, whereby the medicament delivery member sleeve 7 maintains its compressed shape in the event of deformation. With elastic and plastic deformation is here meant such deformation resulting from the compression. The latter may be advantageous in that a user more easily may recognise that the medicament delivery device 1 has been subjected to mechanical shock.

Figure 8:
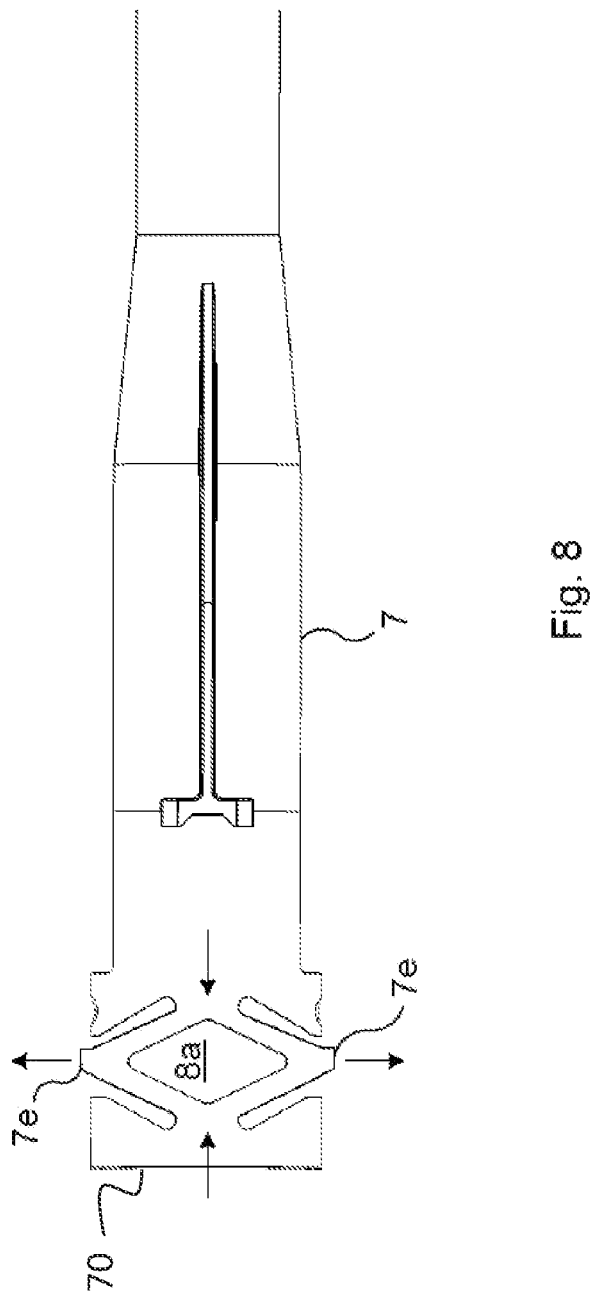
FIG. 8 is a side view of the medicament delivery sleeve member in FIG. 7 in a compressed state.

In the event that the medicament delivery device 1, after medicament administration, when the medicament delivery member sleeve 7 is locked in the extended position, is subjected to an axial force greater than a threshold value, the radial protrusions 7b could be subjected to such a high force that they break, allowing the medicament delivery member sleeve to move distally to its retracted position. However, due to the resilient structure 7d the medicament delivery member sleeve 7 is compressed and therefore expands radially, as shown in FIG. 8, where the opposing axial arrows indicate compression and the radial arrows indicate radial expansion. In particular, the narrow side wall bands 7e are pressed radially outwards by the compression/deformation of the central through-openings 8a. Thereby, the medicament delivery member sleeve 7 will not be able to move to all the way to its retracted position, and the medicament delivery member will not be exposed as it will be maintained covered by the medicament delivery member sleeve 7.

The threshold or threshold value at which the resilient structure deforms so as to expand is a design parameter and depends e.g. on the thickness of the material used for the proximal end portion and on the configuration of the system of through-openings. For example, the resilient structure should not allow so much compression of the medicament delivery member sleeve 7 that it expands radially during normal use, i.e. when applying pressure to the medicament delivery device 1 at the injection site during medicament administration.

It should be noted that according to some variations the safety mechanism 27 is only provided with one of the safety features, e.g. only with the "pre-use" protection, i.e. the proximal flange, or only with the "post-use" protection, i.e. the resilient structure.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A medicament delivery device comprising:
    a medicament delivery member sleeve having a distal end and a proximal end;
    a housing having a longitudinal axis and a proximal opening arranged to slidably receive the medicament delivery member sleeve;
    a flange positioned at the proximal end of the medicament delivery member sleeve, where the flange comprises a distally directed radially flexible arm having an inner surface that abuts an outside surface of the housing adjacent the proximal opening;
    a container driver slidably positioned within the housing and having a locked position and a released position; and
    a driver locking member axially fixed relative to the housing and operationally engaged with the distal end of the medicament delivery member sleeve,
    wherein the container driver is maintained in the locked position by engagement with the driver locking member,
    wherein the medicament delivery member sleeve is axially displaceable inside and relative to the housing between an extended position and a retracted position, and
    wherein movement of the medicament delivery member sleeve from the extended position to the retracted position causes the driver locking member to rotate which allows the container driver to move from the locked position to the released position.

2. The medicament delivery device of claim 1, wherein the container driver is rotationally locked to the housing.

3. The medicament delivery device of claim 1, wherein the container driver comprises locking ribs to mate with grooves on inside of the housing to prevent relative rotation of the container driver relative to the housing.

4. The medicament delivery device of claim 1, wherein the container driver comprises a ledge that is releasably engaged with an inner surface of the driver locking member.

5. The medicament delivery device of claim 4, wherein the rotation of the driver locking member releases the ledge from the inner surface.

6. The medicament delivery device of claim 1, wherein the container driver moves axially and proximally relative to the housing when in the released position.

7. The medicament delivery device of claim 1, further comprising:
    an energy accumulating member that biases the medicament delivery member sleeve in a proximal direction.

8. The medicament delivery device of claim 1, wherein the driver locking member allows the medicament delivery member sleeve to move to a second extended position after the retracted position, where when in the second extended position retraction of the medicament delivery member sleeve is prevented when the driver locking member is in the second extended position.

9. The medicament delivery device of claim 1, further comprising:
    a container holder engaged with the container driver such that proximal axial movement of the container driver causes proximal axial movement of the container holder.

10. The medicament delivery device of claim 9, wherein the engagement of the container holder with the container driver is through an arm located on the container driver.

11. A medicament delivery device comprising:
a medicament delivery member sleeve having a distal end and a proximal end;
a housing having a longitudinal axis and a proximal opening arranged to slidably receive the medicament delivery member sleeve;
a container driver rotationally fixed to the housing; and
a plunger driver locking member having a first state and a second state, where when in the first state the plunger driver locking member is engaged with container driver and when in the second state the plunger driver locking member is disengaged from the container driver,
wherein the proximal end of the medicament delivery sleeve has a resilient structure that expands radially outward relative to the longitudinal axis when the proximal end is compressed, and
wherein axial proximal movement of the container driver causes a transition of the plunger driver locking member from the first state to the second state and starts delivery of medicament from the medicament delivery device.

12. The medicament delivery device of claim 11, wherein the plunger driver locking member comprises a flange that is engaged with an inside surface of the container driver.

13. The medicament delivery device of claim 12, wherein the flange is slidably engaged with a rib on the inside surface of the container driver to maintain the plunger driver locking member in the first state.

14. The medicament delivery device of claim 13, wherein the rib extends in a longitudinal direction and where a length of the rib determines when the delivery of medicament from the medicament delivery device begins.

15. The medicament delivery device of claim 12, wherein disengagement of the flange from the inside surface of the container driver causes the delivery of medicament from the medicament delivery device to begin.

16. The medicament delivery device of claim 11, wherein the container driver is rotationally locked the housing.

17. The medicament delivery device of claim 11, wherein the container driver has locking ribs to mate with grooves on inside of the housing.

18. The medicament delivery device of claim 11, further comprising:
a container holder engaged with the container driver such that proximal axial movement of the container driver causes proximal axial movement of the container holder.

19. The medicament delivery device of claim 18, wherein the engagement of the container holder with the container driver is through an arm located on the container driver.

20. The medicament delivery device of claim 18, wherein needle penetration occurs during the proximal axial movement of the container holder.

* * * * *